United States Patent [19]

Huber et al.

[11] Patent Number: 5,518,790
[45] Date of Patent: May 21, 1996

[54] CONTAINER TO HOLD AROMATIC SUBSTANCES

[75] Inventors: Hans-Peter Huber, Östringen; Hartmut Klocke, Karlsruhe, both of Germany; Herbert Wendel, Sarre-Guemines, France

[73] Assignees: Klocke Verpackungsservice GmbH. AG, Weingarten, Germany; Manka Developpement de Concepts Produits, Colmar, France

[21] Appl. No.: 144,023

[22] Filed: Nov. 1, 1993

[30] Foreign Application Priority Data

Oct. 31, 1992 [DE] Germany ............ 42 36 886.2

[51] Int. Cl.⁶ .................. A61L 9/04; B65D 75/28
[52] U.S. Cl. .......... 428/35.2; 428/35.3; 428/35.4; 428/35.9; 428/36.7; 428/41.3; 428/166; 428/202; 428/215; 428/218; 428/458; 428/461; 428/475.2; 428/476.3; 428/483; 428/516; 428/518; 428/905; 239/55; 239/57; 206/484; 206/484.1
[58] Field of Search ................ 428/35.2, 35.9, 428/35.3, 35.4, 36.5, 35.8, 475.2, 476.3, 458, 461, 483, 516, 518, 520, 905, 40, 192, 166, 202, 66.3, 36.7, 36.6, 215, 218, 319.9; 206/484, 484.1; 239/53, 55, 57; 156/69, 308.4, 322, 76, 229

[56] References Cited

U.S. PATENT DOCUMENTS

| | | | |
|---|---|---|---|
| 2,979,268 | 4/1961 | Brun ............................... | 239/55 |
| 3,083,821 | 4/1963 | Woodson ........................ | 206/47 |
| 3,570,491 | 3/1971 | Sneider .......................... | 128/290 |
| 3,702,677 | 11/1972 | Heffington ..................... | 239/55 |
| 4,055,672 | 10/1977 | Hirsch et al. .................. | 426/127 |
| 4,085,244 | 4/1978 | Stillman ......................... | 206/484 |
| 4,130,245 | 12/1978 | Bryson ........................... | 239/24 |
| 4,145,001 | 3/1979 | Weyenberg et al. ............ | 239/56 |
| 4,157,787 | 6/1979 | Schwarz ......................... | 239/56 |
| 4,161,283 | 7/1979 | Hyman ........................... | 239/55 |
| 4,172,914 | 10/1979 | Festag et al. .................. | 428/35.9 |
| 4,220,244 | 9/1980 | Elmore ........................... | 206/210 |
| 4,285,468 | 8/1981 | Hyman ........................... | 239/55 |
| 4,381,848 | 5/1983 | Kahn ............................... | 229/43 |
| 4,382,513 | 5/1983 | Schirmer et al. .............. | 206/484 |
| 4,405,667 | 9/1983 | Christensen et al. .......... | 428/35.4 |
| 4,407,873 | 10/1983 | Christensen et al. .......... | 428/35.4 |
| 4,407,874 | 10/1983 | Gehrke ........................... | 428/35.2 |
| 4,438,850 | 3/1984 | Kahn ............................... | 206/634 |
| 4,469,258 | 9/1984 | Wright et al. .................. | 229/43 |
| 4,482,513 | 11/1984 | Auletti ............................ | 264/39 |
| 4,497,857 | 2/1985 | Bonis .............................. | 428/35.2 |
| 4,537,305 | 8/1985 | Takanashi ....................... | 206/484 |
| 4,539,259 | 9/1985 | Zuscik ............................ | 428/332 |
| 4,634,614 | 1/1987 | Holzner .......................... | 206/484.1 |
| 4,658,434 | 4/1987 | Murray ........................... | 383/66 |
| 4,660,721 | 4/1987 | Mykleby ......................... | 206/439 |

(List continued on next page.)

FOREIGN PATENT DOCUMENTS

| | | |
|---|---|---|
| 3149508 | 12/1990 | Germany . |
| WO81/00051 | 1/1981 | WIPO . |
| WO82/02700 | 8/1982 | WIPO . |
| WO84/03360 | 8/1984 | WIPO . |
| 89/07959 | 9/1989 | WIPO . |

*Assistant Examiner*—Rena L. Dye
*Attorney, Agent, or Firm*—Fisher, Christen & Sabol

[57] ABSTRACT

A container to hold aromatic substances which can be sealed aroma-tight with a composite film consisting of several laminae. The composite film on the top of the container is made up of an aroma-tight outer film having at least two laminae and an aroma-permeable inner film which is detachably bonded to the outer film by means of a bonding agent. The outer film can be applied onto the inner film or membrane film, which consists of at least two permanently bonded laminae, whereby the lamina adhering to the container is made of polyethylene and the third or top lamina is made of a polymer materialwhich has a different density. The surface structure of the side of the membrane film facing away from the container is selected in such away that the entire membrane film stays on the container when the outer film (16) is pulled off.

21 Claims, 2 Drawing Sheets

U.S. PATENT DOCUMENTS

| | | | |
|---|---|---|---|
| 4,698,247 | 10/1987 | Murray et al. | 428/35.2 |
| 4,724,961 | 2/1988 | Shimoyamada et al. | 206/439 |
| 4,731,268 | 3/1988 | Murray, Jr. et al. | 428/35.2 |
| 4,766,018 | 8/1988 | Hinrichsen et al. | 428/35.9 |
| 4,771,935 | 9/1988 | Hekal | 229/3.5 |
| 4,771,937 | 9/1988 | Kamada et al. | 229/123.1 |
| 4,785,937 | 11/1988 | Tamezawa et al. | 206/484 |
| 4,793,555 | 12/1988 | Lee et al. | 239/6 |
| 4,849,606 | 7/1989 | Martens, III et al. | 219/271 |
| 4,856,649 | 8/1989 | Inoue | 209/204 |
| 4,884,694 | 12/1989 | Sengewald | 206/484 |
| 4,889,731 | 12/1989 | Williams, Jr. | 206/484.1 |
| 4,905,838 | 3/1990 | Suzuki et al. | 206/631 |
| 4,923,119 | 5/1990 | Yamamoto et al. | 239/55 |
| 4,943,780 | 7/1990 | Redding | 428/35.9 |
| 5,011,019 | 4/1991 | Satoh et al. | 206/530 |
| 5,062,569 | 11/1991 | Hekal | 206/484 |
| 5,132,151 | 7/1992 | Graney | 428/40 |
| 5,160,767 | 11/1992 | Genske et al. | 428/35.9 |
| 5,161,688 | 11/1992 | Muchin | 206/484 |
| 5,178,293 | 1/1993 | Suzuki et al. | 220/359 |
| 5,197,618 | 3/1993 | Goth | 215/232 |
| 5,199,595 | 4/1993 | Muggli et al. | 428/35.9 |
| 5,230,867 | 7/1993 | Kunze et al. | 422/123 |
| 5,279,421 | 1/1994 | Gouge et al. | 206/484 |
| 5,281,453 | 1/1994 | Yamada et al. | 428/35.7 |
| 5,341,922 | 8/1994 | Cerwin et al. | 206/63.3 |
| 5,348,752 | 9/1994 | Gorlich | 426/129 |
| B1 4,884,694 | 7/1991 | Sengewald | 206/484 |

CONTAINER TO HOLD AROMATIC SUBSTANCES

BACKGROUND OF THE INVENTION

1. Field of the Invention

The invention relates to a container to hold aromatic substances which can be sealed aroma-tight by means of a composite film which consists of several laminae, whereby the composite film on the top of the container is made up of an aroma-tight outer film which has at least two laminae and an aroma-permeable inner film which is detachably bonded to the outer film by means of a bonding agent.

2. Background Art

German Patent No. 3,149,508 discloses the sealing of a fragrance pouch with two aroma-tight film surfaces joined together at the edges in order to enclose a fragrance, whereby the film surface on the pouch side is made of a double layer which consists of an aroma-permeable inner layer and an aroma-tight outer layer. The edges can be sealed or fused.

Moreover, a container to hold fragrant substances is known from German Patent No. 3,490,012, whereby this container has a chamber with a wall made of polymer material which, after a top film is pulled off, allows the diffusion of the active substance vapors into the surrounding atmosphere. The surface of the polymer, vapor-permeable bottom wall is covered by a paper sheet which has a thickness of between 20 and 100 μ and a density of between 20 and 100 g/m². A second polymer wall laminated with aluminum adheres to this paper sheet. In order to release the fragrance, the user can tear open the protective layer which consists of aluminum and polymer material, whereby the paper is split in the middle. The paper sheet positioned between the two polymer layers has the substantial disadvantage that, over a prolonged storage period, the paper sheet already becomes soaked with fragrance before the top cover film is pulled off, as a result of which this fragrance diffuses laterally to the outside through the paper sheet at the seam between the two laminae made of polymer material, so that a large portion of the fragrance is already lost before the item is put into use. This translates into a very short shelf life for the sealed pouch.

BROAD DESCRIPTION OF THE INVENTION

The main objective of the invention is to provide a composite film to be used for a container to hold aromatic substances, whereby this container is compatible with its contents and it ensures a long shelf life of these contents.

The main objective is achieved according to the invention in that the outer film can be applied onto the inner film or membrane film which consists of at least two permanently bonded laminae, whereby the lamina adhering to the container is made of polyethylene and the third or top lamina is made of a polymer material. Thus, an aroma-tight composite film is created in a simple manner and the fragrance is prevented from diffusing laterally to the outside through the layer between the barrier layer and the container, even after a prolonged storage period. For this purpose, it is advantageous for the third lamina of the entire composite film arrangement, that is to say, the lamina belonging to the membrane, to be made of foamed polypropylene, whereby the specific density (kg/cm²) of the third or top lamina is selected in such a way that the membrane film made up of the two laminae stays on the container when the outer film is pulled off.

On the basis of another embodiment of the composite film according to the invention, the third lamina or foamed polypropylene is permanently bonded to the polyethylene below it, at least in the edge area, and the foamed polypropylene and/or the laminae below it are crimped, at least in the edge area of the permanent bond. The composite film which consists of four laminae, or, if one counts the adhesive laminate, of seven laminae, creates an aroma-tight composite laminate with excellent tightness properties so that the shelf life can be considerably extended in comparison to the generally known composite laminates. The crimped edge area of one or more laminae prevents diffusion through the otherwise aroma-permeable laminae below the barrier layer as long as the outer film has not been pulled off.

In another embodiment of the invention, it is advantageous when the foamed polypropylene is crimped in the area of the permanent bond by means of a heat treatment.

Finally, according to a preferred embodiment of the proposal according to the invention, it is recommended to permanently bond the foamed polypropylene to the polyethylene below it over the entire surface by means of an adhesive lamina and only to crimp it in the edge area and/or especially in the area of the adhesion or sealing site.

It is of special significance for the present invention that the outer film consists of two laminae permanently bonded to each other, whereby one of the laminae is formed as an aroma-tight barrier layer and the other lamina is made of a flexible or elastic material, especially of the polyamide material. By using the foamed polypropylene, an optimal sealing of the container is in addition achieved when the outer film which consists of two laminae is bonded to the aroma-permeable inner film because this material, especially in the edge area, does not absorb the aromatic substance, particularly not when this edge area is crimped. As a result, the aroma-tight seal is further improved and it is ensured that the aromatic substance cannot diffuse through the individual laminae below the barrier layer. The top lamina made of flexible or elastic material ensures that the barrier layer is not damaged when the top layer is pulled off.

In conjunction with the embodiment and the arrangement according to the invention, it is advantageous for the barrier layer to be made of a metal, especially of an aluminum material.

Moreover, it is also advantageous when the aroma-tight barrier layer is permanently bonded to the adjacent lamina over the entire surface.

It is also advantageous when the container to hold aromatic substances is made of two laminae bonded to each other over the entire surface, whereby one of the laminae of the container is made of polyethylene and the other lamina, the one on the outside, is made of a polymer material, preferably polyester or polypropylene, and when the individual laminae are each permanently bonded to each other over the entire surface by means of an adhesive lamina. As a result, a flawless, high-strength bond is created between the individual laminae.

Moroeever, it is advantageous when the outer film is fused with the inner film or membrane film in the edge area or else is bonded by means of the adhesive lamina. As a result, at the site of adhesion, the barrier layer can be pulled away from the lamina below, which is bonded to the container, so that fragrance can diffuse to the outside through the parts which are not crimped.

An additional benefit contained in another embodiment of the composite film according to the invention is that the outer film is fused to the inner film or membrane film over the entire surface or else it is bonded by means of the adhesive lamina, so that in the edge area, there is a separation line for an opening tab which is designed in such a way that it can be used to pull the outer film away from the inner film, so that the bond between the inner film and outer film, that is to say, the polypropylene lamina, can be separated in the area of the adhesive lamina from the polypropylene lamina over the entire surface. Thanks to the advantageous arrangement of the opening tab, the first lamina, which functions as a support film can be pulled off with the barrier layer without damaging the latter. Since the barrier layer has a considerably higher cohesive integrity than the polypropylene material, it adheres completely to the bottom lamina, which functions as a membrane.

In another embodiment of the invention, it is advantageous when the edge area of the underside of the outer film or second lamina has a protective layer, especially a strip of coating, in order to prevent a bonding of the underside of the second lamina with the top of the third lamina, and when the second lamina of the outer film consists of a non-metallic material, especially hydrolyzed vinyl acetate and/or ethylene and/or copolymer material (EVOH and EVA), and is bonded to the first lamina, which consists of a flexible material, especially one made of polyamide or polypropylene. In this manner, a recyclable material is obtained.

As described above, it is advantageous when the individual laminae are permanently bonded to each other over the entire surface by employing a two-component adhesive on the basis of PU, an acrylic adhesive or a coextrusion process.

An additinal benefit found in another embodiment of the container according to the invention is that the two films are rendered transparent through heat treatment of the polypropylene material or membrane film or polyethylene film, so that the substance held in the container is visible through the two laminae when the outer film has been pulled off. Making the substance visible can also be achieved when the substance is placed into the container, e.g., when it comes into contact with the lamina.

It is also advantageous when at least the top lamina forming the container has approximately the same properties or density ($kg/cm^2$) as the aroma-permeable lamina which functions as a membrane and which also seals the container, allowing aromatic substances to pass through, and when the two laminae are fused together.

An essential, advantageous embodiment is achieved in that the adhesive laminant between the barrier layer or outer film and the polypropylene adheres less strongly to the polypropylene than does the adhesive laminant between the polypropylene and the polyethylene.

It is further advantageous when the density of the material of the barrier layer is greater than the density of the material of the top lamina or polypropylene, and when the density of the material of the top lamina of the container or polypropylene is less than the density of the material of the bottom lamina or polyethylene, so that the density of the bottom lamina of the membrane and of the top lamina adhering to the container is the same.

Moreover, it is advantageous when the first lamina of the composite film or of the container has a thickness between 12 μ and 80 μ, the second lamina has a thickness between 9 μ and 50 μ, the third lamina has a thickness between 33 μ and 60 μ, the fourth lamina has a thickness between 50 μ and 150 μ, the fifth lamina has a thickness between 50 μ and 100 μ and the sixth lamina has a thickness between 250 μ and 500 μ.

In addition, it is also especially advantageous when the first lamina of the composite film or of the container has a thickness between 20 μ and 30 μ, the second lamina has a thickness between 12 μ and 18 μ, the third lamina has a thickness between 28 μ and 38 μ, the fourth lamina has a thickness between 70 μ and 80 μ, the fifth lamina has a thickness between 70 μ and 80 μ and the sixth lamina has a thickness between 320 μ and 380 μ.

Very good results have been achieved when the first lamina of the composite film or of the container has a thickness between 24 μ and 26 μ, the second lamina has a thickness between 14 μ and 16 μ, the third lamina has a thickness between 32 μ and 34 μ, the fourth lamina has a thickness between 74 μ and 76 μ, the fifth lamina has a thickness between 74 μ and 76 μ and the sixth lamina has a thickness between 345 μ and 355 μ.

BRIEF DESCRIPTION OF THE DRAWINGS

Additional advantages and details of the invention are explained in the claims and in the description, and are also illustrated by the Figures, whereby it should be pointed out that all of the individual characteristics and all of the combinations of the individual characteristics are essential to the invention.

In the drawings.

DETAILED DESCRIPTION OF THE INVENTION

Figure 1:
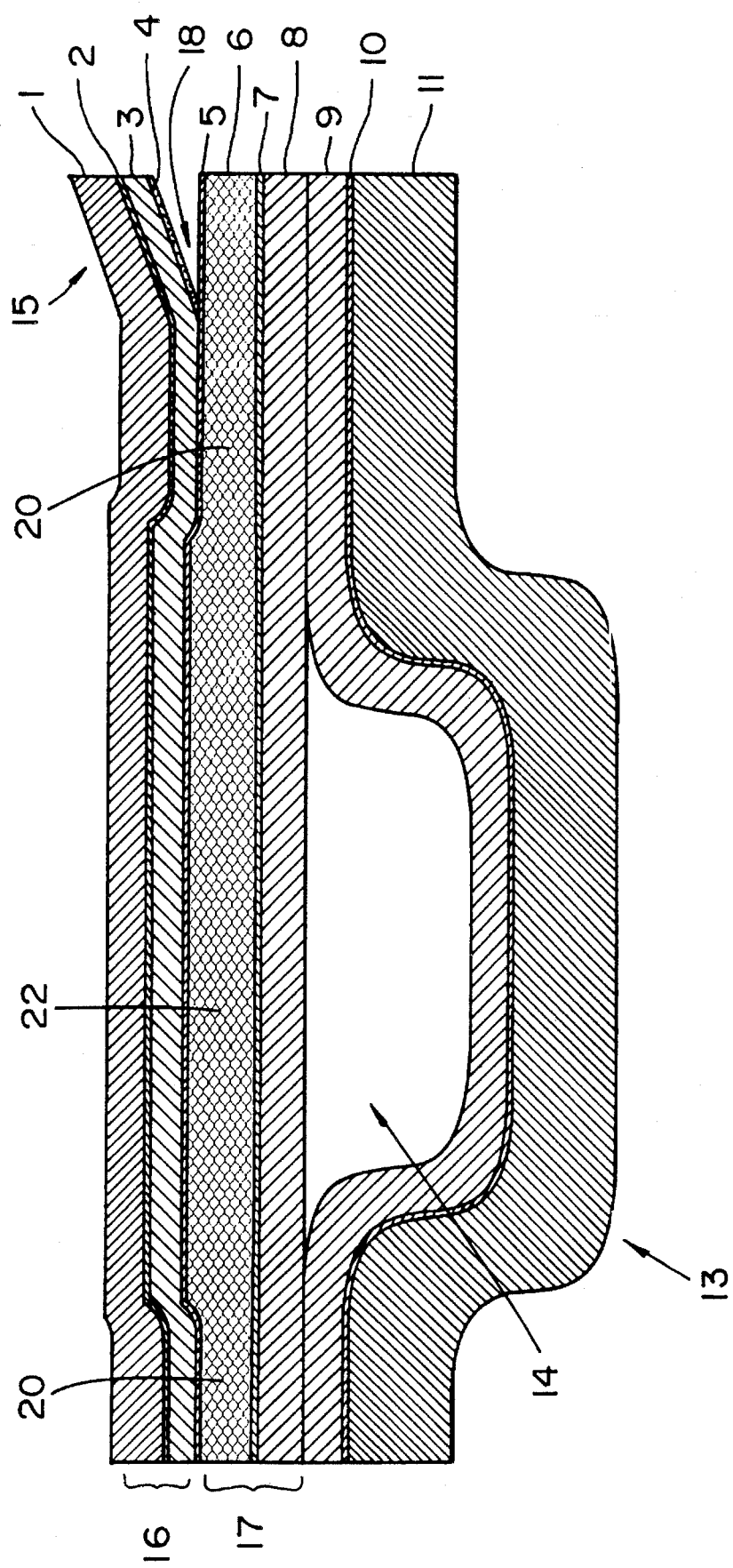
FIG. 1 is a cross sectional view of a container to hold aromatic substances which can be sealed so as to be aromatight by means of a composite film consisting of several laminae.

In the drawing, FIG. 1 shows a container 13 to hold aromatic substances 14 which can be sealed by means of a composite film 15 which consists of several laminae. In the embodiment according to FIG. 1, the composite film 15, including the container 13, consists of a total of six laminae, 1, 3, 6, 8, 9, 11. If one also counts the adhesive laminant 2, 5, 7, 10 between the laminae, then the entire composite film arrangement 15, including the container 13, consists of ten laminae.

An outer film 16 is made up of the two permanently bonded laminae, 1, 3, whereby one of the laminae or the bottom lamina 3 can function as an aroma-tight barrier layer and the other lamina or top lamina 1 can be made of an elastic or flexible material, especially polyamide material or else, for example, polypropylene.

The first lamina 1 ensures that the barrier layer 16 formed as a composite film does not tear while it is being pulled off, so that it can be removed in a simple manner, in order to expose the membrane film 17 designed as an inner film and to make it possible for an aromatic substance 14 held in container 13 to diffuse.

In the entire composite film arrangement 15, the second lamina 3 is made of an aroma-tight material.

The third lamina 6 as counted from the top can be made of a relatively soft polymer material, preferably of a foamed polypropylene. In a special approach involving incorporation into the entire composite film arrangement 15, as will be described below, this lamina has very good tightness properties and constitutes an advantageous bond between the two laminae 3 and 8.

The third lamina or foamed polypropylene 6, together with the underlying lamina 8 bonded to it, form the inner film or membrane film 17. The lamine 8 can consist of polyethylene.

The density of the material of the bottom lamina 3 of the barrier layer 16 is advantageously greater than the density of the material of the third lamina or polypropylene 6. This makes it possible to easily separate the barrier layer 16 from the membrane film 17, while it is also ensured that the third lamina 6 made of polypropylene, which is located between the barrier layer 16 and the membrane film 17, is not split but rather that separation occurs along the adhesive laminant 5.

The barrier layer 3 can be made of a metal, in particular of an aluminum material. However, for environmental reasons, it is advantageous when the barrier layer 3 is made of a non-metallic material. Thus, for example, the barrier layer 3 can be made of a hydrolyzed vinyl acetate and/or ethylene and/or copolymer material (EVOH and EVA), and it can be bonded to the first lamina 1, which can consist of polyamide or polypropylene, as a result of which, as already mentioned, the tear resistance of the barrier layer 3 is considerably improved. The polyvinyl alcohol content of EVOH gives it very good barrier properties and its ethylene content accounts for very good heat and water resistance.

The aroma-tight barrier layer 3 is permanently bonded to the adjacent lamina 1 over the entire surface. The individual laminae 1, 3 and 6, 8 and 9, 11 can each be permanently bonded to each other over the entire surface by employing an adhesive lamina, e.g., a two-component adhesive on the basis of PU, an acrylic adhesive or a coextrusion process.

After being filled with the aromatic substance 14, the container 13 is sealed so as to be aroma-tight by the outer film or barrier layer 16 and by a membrane film 17 consisting of two laminae 6, 8.

The third lamina 6—with respect to the entire composite film arrangement—which belongs to the membrane film 17 is made of a foamed polypropylene and permanently bonded to a fourth lamina 8 made of polyethylene by means of the adhesive lamina 7. The two laminae 6, 8 which make up the membrane film 17 keep the container sealed, even after the outer film 16 has been pulled off.

The bottom lamina 8 which belongs to the membrane film 17 is fused and thus undetachably bonded to the top or fifth lamina 9 which adheres to the container 13.

The container 13 to hold aromatic substances 14 consists of the two laminae 9 and 11 which are bonded to each other over the entire surface, whereby the fifth lamina 9 of the container 13 is made of polyethylene and the sixth or outer lamina 11 is made of a polymer material, preferably polyester or polypropylene. The two laminae 9, 11, which form the container 13, are bonded to each other over the entire surface by means of an adhesive lamina 10.

The top lamina 9, which forms the container 13, has approximately the same properties or density (kg/cm$^2$) as the aroma-permeable fourth lamina 8 which functions as a membrane and seals the container 13. As a result, the two laminae can be easily fused together and thus permanently bonded.

Moreover, it is very advantageous when the adhesive laminant 5 between the barrier layer or outer film 16 and the polypropylene 6 adheres less strongly than does the adhesive lamina 7 between the polypropylene 6 and the polyethylene 8.

The specific density (kg/cm$^2$) of the second or top lamina 3 is selected in such a way that the entire membrane film 17 stays on the container 13 when the outer film 16 is pulled off, i.e., that the specific density (kg/cm$^2$) of the second lamina 3 is greater than the specific density (kg/cm$^2$) of the third lamina 6.

The aroma-tight barrier layer 3 is permanently bonded to the adjacent lamina 1 over the entire surface. The individual laminae 1, 3 and 6, 8 and 9, 11—also explained in greater detail below—are each permanently bonded to each other over the entire surface by an adhesive lamina 2, 5, 7, 10.

Each of the individual laminae 1, 3 and 6, 8 and 9, 11 can be permanently bonded to each other over the entire surface by employing a two-component adhesive, an acrylic adhesive or a coextrusion process.

In order to assure a long shelf life of the substance 14 sealed in container 13, when the barrier layer 16 is bonded to the membrane film 17, at least the edge area of the third lamina or polypropylene 6 and/or the laminae 8, 9 are crimped and permanently bonded by means of the adhesive lamina. The crimped part 20 of the lamina 6 is indicated in FIG. 1 by a step. It prevents the substance held in the container 13 from diffusing to the outside through the interstice formed by the polypropylene 6 between the lamine 3 and the lamine 8.

Furthermore, it is possible to seal the lateral faces of the laminae 6, 8, 9 or to provide them with a barrier layer so that, when the container 13 is in the closed state, no fragrance can escape to the outside via the lateral faces of the laminae 6, 8, 9. Moreover, the top barrier layer can be drawn down over the lateral faces of the laminae 6, 8, 9 which lie below it. Normally, however, the crimped edge area of the lamina 6 will already have ensured an adequate tightness, so that none of the fragrance can diffuse to the outside as long as the lamina 3 has not been pulled away from lamine 6, especially since these laminae cannot become soaked when they are in the sealed state.

The adhesive laminante 5, 7 provided on both sides of the polypropylene 6 can be of such a nature that it additionally prevents diffusion to the outside.

As seen in FIG. 1, there is a chevron-shaped gap or separation line 18 in the edge area of the third lamina 6 so that the section of the two laminae 1, 3 located in the edge area forms a tab or ring 19 by means of which the barrier layer 16 can be pulled off. In the gap 18, the underside of the lamina 3 can be provided with a protective layer 4, especially a flexographic print, a strip of silicone or red silicone coating, so that this part of the lamina 3 does not bond to the part of the lamine 6 below it and, especially while it is being pulled off, the two top laminae 1 and 3 can be pulled off together with the adhesive lamina 5 from the surface of the third lamine 6 or foamed polypropylene without damaging it. Only in the edge area does the laminating adhesive lamina 5 remain on the surface of the polypropylene 6.

When the fragrance is to be activated, the outer film 16 merely has to be pulled off by means of the tab 19, whereby the separation line runs on the plane of the adhesive lamina 5 or along the underside of the adhesive lamina 5. Now the fragrance can pass through the laminae 8 and 6. Since a middle part 22 of the lamina 6 located above the recess in the container 13 was not crimped, the fragrance can be released at a constant diffusion rate through the two laminae 6, 8.

Figure 2:
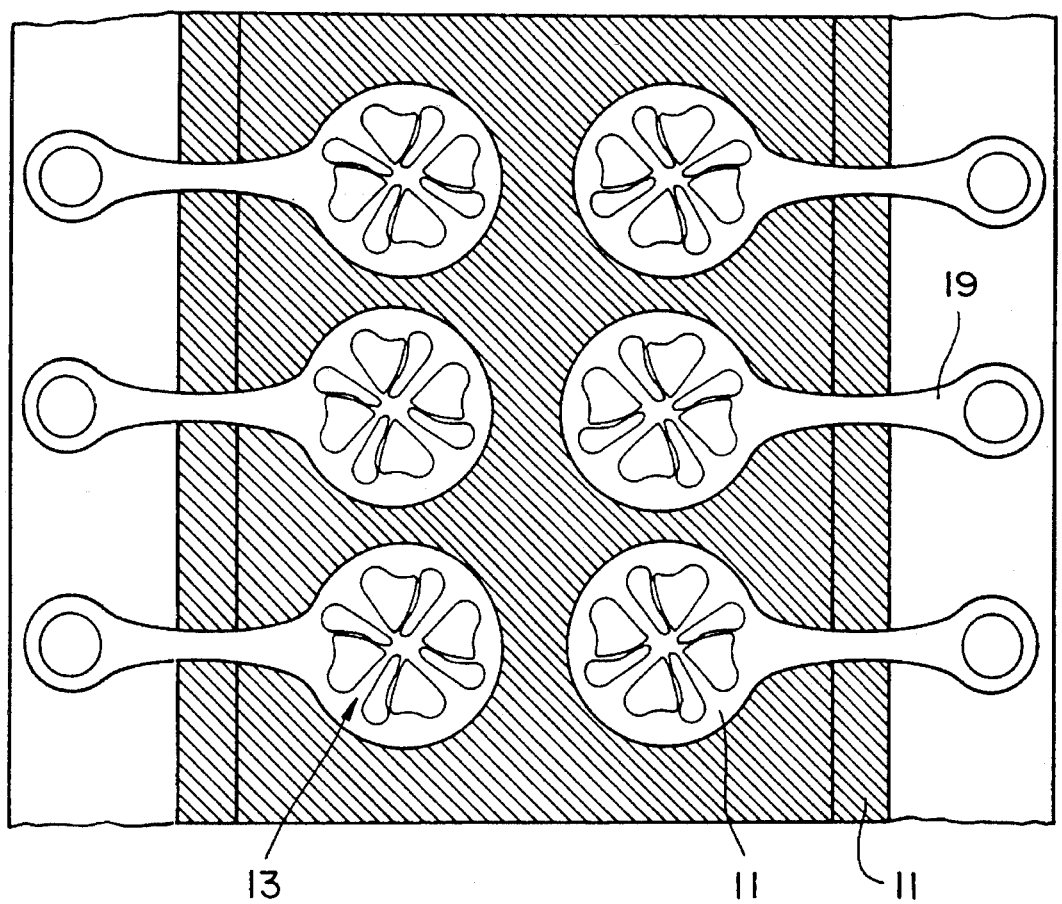
FIG. 2 is a top view of several containers to hold aromatic substances which are connected to each other by means of a film.
Figure 3:
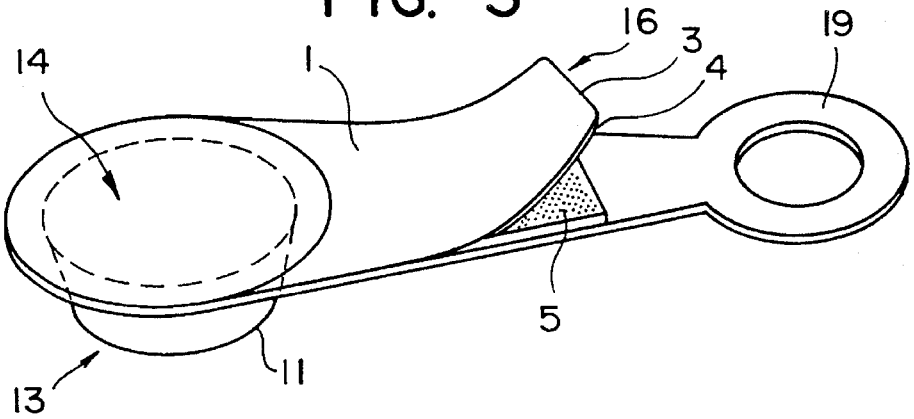
FIG. 3 is a perspective view of a container with an outer film that is partially pulled away.

In FIG. 2, during the manufacturing process, several containers 13 are connected to each other by means of a film, for example, the bottom film or lamina 11, so that they can be handled as multiple packaging. These containers 13 can be punched out or else removed from the film 11 by means of perforation (not shown here).

Furthermore, the two bottom laminae 9, 11 can be extended to the sides of the container in such a manner that the protruding part can be shaped as a ring 19, by means of which the container 13 can be hung, for example, on a hook.

Reference Numbers 1. first lamina, Pa polyamide, support lamina
2. adhesive lamina
3. second lamina, barrier layer consists of metal, especially aluminum
4. protective lamina, flexographic print, strip of silicone, red
5. adhesive lamina, bonding agent
6. third lamina, foamed polypropylene, pp=polymer
7. adhesive lamina, bonding agent
8. fourth lamina, polyethylene
9. fifth lamina, polyethylene
10. adhesive lamina
11. sixth lamina, polyester, polypropylene
13. container
14. aromatic substance
15. composite film
16. outer film, barrier layer, first and second laminae (1,3) [lamina (13) can be hydrolyzed vinyl acetate, ethylene and copolymer of EVOH and EVA] and can likewise be used as a barrier layer
17. inner film, membrane film, third and fourth laminae (6, 8)
18. separation line
19. tab, loop
20. crimped part
22. uncrimped part

What is claimed is:

1. A container (13) to hold aromatic substances (14) which is sealed aroma-impermeable by means of a composite film (15) sealed to the container, the composite film (15) consisting of several laminae, whereby the composite film (15) on the top of the container is made up of an aroma-impermeable outer film (16) having at least two laminae (1, 3) including a barrier layer, and an aroma-permeable inner film (17) which is detachably bonded to the outer film (16) by means of a bonding agent (5) which forms an adhesive laminate, the outer film (16) being applied onto the inner film or membrane film (17), consisting of at least two permanently bonded laminae (6, 8), whereby the lamina (8) adhering to the container is made of polyethylene and the third or top lamina (6) is made of foamed polypropylene, the adhesive lamina (5) between the barrier layer or outer film (16) and the polypropylene lamina (6) adhering less strongly to the polypropylene (6) than does the adhesive lamina (7) between the polypropylene (6) and the polyethylene (8), whereby the specific density (kg/cm$^2$) of the third or top lamina (6) is selected so that the membrane film (17) made up of the two laminae (6, 8) stays on the container (13) when the outer film (16) is pulled off.

2. The container according to claim 1 wherein the third lamina or foamed polypropylene (6) is permanently bonded to the polyethylene (8) below it, at least in the edge area, and the foamed polypropylene (6), or the laminae (8, 9), or both the polyethylene (6) and the laminae (8, 9) below it are crimped at least in the edge area which has been permanently bonded.

3. The container according to claim 2 wherein the foamed polypropylene (6) is crimped in the area which has been permanently bonded by means of a heat treatment.

4. The container according to claim 1 wherein the foamed polypropylene (6) is permanently bonded to the polyethylene (8) below it over the entire surface by means of the adhesive lamina (7) and is only crimped in the area selected from the edge area, the adhesion or sealing site or a combination thereof.

5. The container according to claim 1 wherein the outer film (16) consists of two laminae (1, 3), permanently bonded to each, whereby the lamina (3) is formed as an aroma-impermeable barrier layer and the other lamina (1) is made of a flexible or elastic material.

6. The container according to claim 5 wherein the barrier layer (3) is made of aluminum metal.

7. The container according to claim 6 wherein the other lamina (1) is made of a polyamide material.

8. The container according to claim 5 wherein the aroma-impermeable barrier layer (3) is permanently bonded to the adjacent lamina (1) over the entire surface.

9. The container according to claim 1 wherein the container (13) to hold aromatic substances (14) is made of two laminae (9, 11) bonded to each other over the entire surface, whereby inner lamina (9) of the container (13) is made of polyethylene and outer lamina (11) is made of polyester or polypropylene.

10. The container according to claim 9 wherein the individual laminae (1, 3 and 6, 8 and 9, 11) are each permanently bonded to each other over the entire surface by means of an adhesive lamina (2, 5, 7, 10).

11. The container according to claim 1 wherein the outer film (16) is fused with the inner film or membrane film (17) in the edge area or else is bonded by means of the adhesive lamina (5).

12. The container according to claim 1 wherein the outer film (16) is fused over the entire surface with the inner film or membrane film (17) or else it is bonded by means of the adhesive lamina (5), whereby in the edge area, there is a separation line (18) for an opening tab (19) which is designed in such a way that it can be used to pull the other film (16) away from the inner film (17) and the bond between the inner film (17) and outer film (16) in the area of the adhesive lamina (5) can be separated over the entire surface from the polypropylene lamina (6).

13. The container according to claim 1 wherein edge area of the underside of the outer film (16) or of the second lamina (3) has a protective layer or a strip of coating (4), in order to prevent a bonding of the underside of the second lamina with the top of the third lamina (6).

14. The container according to claim 1 wherein the second lamina (3) of the outer film (16) consists of a non-metallic material selected from the group consisting of hydrolyzed vinyl acetate, ethylene, copolymer composed of ethylene vinyl alcohol and ethylene vinyl acetate, and combinations thereof, and is bonded to the first lamina (1).

15. The container according to claim 14 wherein the first lamina (1) is a flexible material selected from the group consisting of polyamide and polypropylene.

16. The container according to claim 1 wherein the individual laminae (1, 3 and 6, 8 and 9, 11) are permanently bonded to each other over the entire surface by employing a two-component adhesive, an acrylic adhesive or a coextrusion process.

17. The container according to claim 1, the container (13)

to hold aromatic substances (14) is made of inner lamina (9) and outer lamina (11) bonded to each other over the entire surface, wherein inner lamina (9) forming the container has approximately the same properties or density (kg/cm$^2$) as the aroma-permeable lamina (8) which functions as a membrane and also seals the container (13) and allows aromatic substances to pass through, and in that the two laminae (8, 9) are fused together.

18. The container according to claim 1 wherein the density of the material of the barrier layer (3) is greater than the density of the material of the top lamina or polypropylene (6), and in that the density of the material of the top lamina or polypropylene (6) is less than the density of the material of the bottom lamina or polyethylene (8).

19. The container according to claim 1 wherein the first lamina (1) of the composite film or of the container (13) has a thickness between 12 μ and 80 μ, the second lamina (3) has a thickness between 9 μ and 50 μ, the third lamina (6) has a thickness between 33 μ and 60 μ, the fourth lamina (8) has a thickness between 50 μ and 150 μ, the fifth lamina (9) has a thickness between 50 μ and 100 μ and the sixth lamina (11) has a thickness between 250 μ and 500 μ.

20. The container according to claim 1 wherein the first lamina (1) of the composite film or of the container (13) has a thickness between 20 μ and 30 μ, the second lamina (3) has a thickness between 12 μ and 18 μ, the third lamina (6) has a thickness between 28 μ and 38 μ, the fourth lamina (8) has a thickness between 70 μ and 80 μ, the fifth lamina (9) has a thickness between 70 μ and 80 μ and the sixth lamina (11) has a thickness between 320 μ and 380 μ.

21. The container according to claim 1 wherein the first lamina (1) of the composite film or of the container (13) has a thickness between 24 μ and 26 μ, the second lamina (3) has a thickness between 14 μ and 16 μ, the third lamina (6) has a thickness between 32 μ and 34 μ, the fourth lamina (8) has a thickness between 74 μ and 76 μ, the fifth lamina (9) has a thickness between 74 μ and 76 μ and the sixth lamina (11) has a thickness between 345 μ and 355 μ.

* * * * *